United States Patent [19]

Hauser et al.

[11] Patent Number: 5,132,440

[45] Date of Patent: Jul. 21, 1992

[54] PROCESS FOR THE PRODUCTION OF PROGESTERONE DERIVATIVES

[75] Inventors: Helmut Hauser, Vericruz, Mexico; Hans D. Berndt, Berlin, Fed. Rep. of Germany

[73] Assignee: Schering Aktiengesellschaft, Berlin & Bergkamen, Fed. Rep. of Germany

[21] Appl. No.: 720,822

[22] PCT Filed: Sep. 6, 1990

[86] PCT No.: PCT/DE90/00688

§ 371 Date: Jul. 15, 1991

§ 102(e) Date: Jul. 15, 1991

[87] PCT Pub. No.: WO91/04265

PCT Pub. Date: Apr. 4, 1991

[30] Foreign Application Priority Data

Sep. 14, 1989 [DE] Fed. Rep. of Germany ....... 3931064

[51] Int. Cl.$^5$ ................................................. C07J 7/00
[52] U.S. Cl. .................................... 552/596; 552/597; 552/598
[58] Field of Search ..................... 552/596, 597, 598

[56] References Cited

U.S. PATENT DOCUMENTS 4,585,590 4/1986 Van Rheenen ................. 260/239.55
4,831,131 5/1989 Van Rheemen ................... 540/87

FOREIGN PATENT DOCUMENTS 0153001 8/1985 European Pat. Off. .

OTHER PUBLICATIONS

Gasc, J. C. and L. Nédélec, "A New Approach to Corticoid Total Synthesis", *Tetrahedron Letters*, No. 22, pp. 2005-2008 (1971).

Ruggieri et al., "17-Hydroxypregnanes from Androstane Compounds," J. Amer. Chem. Soc., Band. 81 (Nov. 1959).

*Primary Examiner*—Marianne Cintins
*Assistant Examiner*—Kimberly J. Kestler
*Attorney, Agent, or Firm*—Millen, White & Zelano

[57] ABSTRACT

A process for the production of progresterone derivatives of general formula I

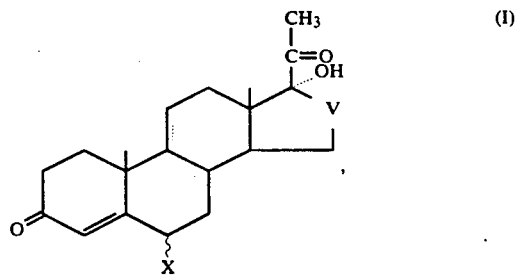

in which
⋯⋯ symbolizes a single bond or a double bond,
X represents a hydrogen atom, a fluorine atom or a methyl group and
V means a methylene group, an ethylene group, an ethylidene group or a vinylidene group, is described.

4 Claims, No Drawings

PROCESS FOR THE PRODUCTION OF PROGESTERONE DERIVATIVES

The invention relates to a process for the production of progesterone derivatives of general formula I

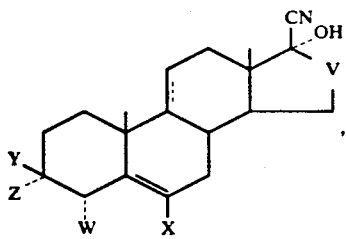
(I)

in which
----- symbolizes a single bond or a double bond,
X represents a hydrogen atom, a fluorine atom or a methyl group and
V means a methylene group, an ethylene group, an ethylidene group or a vinylidene group, which is characterized in that a nitrile of the general formula II

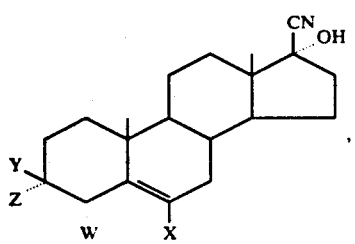
(II)

in which
----- X and V have the above-mentioned meaning and in which Y and Z together are an alkylenedioxy group with 2 to 6 carbon atoms and W represents a hydrogen atom or in which
Y symbolizes an alkyloxy group with up to 4 carbon atoms, a benzyl group or an acyloxy group with 2 to 8 carbon atoms, and Z and W represent two hydrogen atoms or together mean a carbon-carbon bond,
with a Grignard reagent of the general formula III $$Ch_3-Mg-Z \quad (III),$$

in which Z symbolizes a chlorine atom or a bromine atom, is reacted and the intermediate products formed are hydrolyzed by acids.

By an alkylenedioxy group Y and Z of the nitriles of the general formula II is to be understood, for example, a 1,2-ethylenedioxy group, a 1,3-propylenedioxy group, a 2,2-dimethyl-1,3-propylenedioxy group or a 2,3-butylenedioxy group.

Suitable alkoxy groups Z are, for example, the methoxy group, the ethoxy group, the isopropyloxy group or the tertbutyloxy group.

Suitable acyloxy groups are, among others, the acetoxy group, the propionyloxy group, the dimethylacetoxy group, the trimethylacetoxy group and the benzoyloxy group.

The Grignard reagent necessary for carrying out the process according to the invention can be produced in the usual way, for example by methyl chloride or methyl bromide in an either such as diethyl ether, diisopropyl ether, dibutyl ether, 1,2-dimethoxyethane or tetrahydrofuran being reacted with magnesium chips. Because of its relatively low boiling point and its not too low flash point, tetrahydrofuran is especially suitable. These Grignard reagents can be used directly for the reaction with the nitriles of general formula II. But the ether suitably is largely removed by distillation before the reaction and replaced by toluene. (It is noted that in comparison with benzene, toluene has the advantage of substantially lower toxicity, and in comparison with xylenes, toluene has the advantage of a low boiling point). It not has only the advantage that a large part of the ether can be recovered problem-free but also that the reaction can be performed under mile conditions and the working up of the reaction mixture is greatly facilitated.

To carry out the reaction, at least 4 moles of Grignard reagent is necessary to reach high yields in the process product. The reaction is performed at a temperature of $-20°$ C. to $+10°$ C.—preferably at $-5°$ to $+5°$ C. Under these conditions, the reaction time is about 30 to 180 minutes.

After the reaction has been completed, the reaction mixture, as in the case of Grignard reactions, is usually decomposed. This decomposition can take place, for example, with an aqueous solution of tetrasodium salt of ethylenediaminetetraacetic acid; however, this reagent is somewhat expensive. The decomposition of the reaction mixture with aqueous ammonium chloride solution has been proven quite suitable and problem-free.

After the decomposition has been completed, the toluene can be removed by steam distillation and an intermediate product is obtained which consists of a mixture of the progesterone derivative of the general formula I and the imino compounds of formulas IV and V

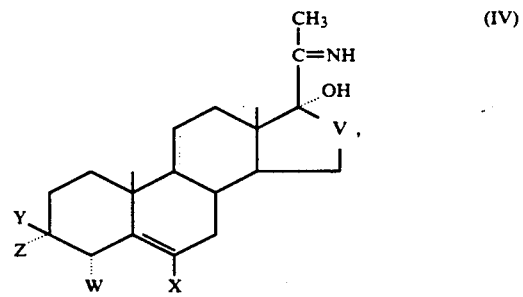
(IV)

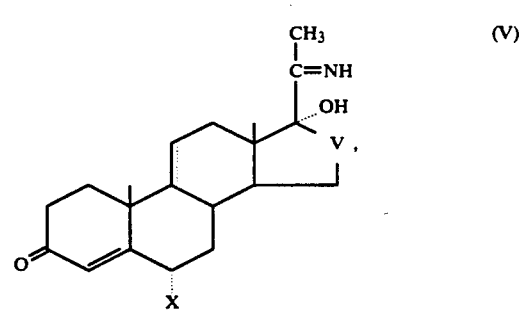
(V)

(in these formulas, -----, X, Y, Z, W and V have the above-mentioned meaning).

This product can be hydrolyzed problem-free by acids to the progesterone derivatives of the general formula I.

This hydrolysis can be performed, for example, so that the intermediate product dissolves in a lower alcohol—such as methanol, ethanol or isopropanol, mixed with an acid, such as hydrochloric acid, sulfuric acid or p-toluenesulfonic acid and heated. After the reaction has been completed, the reaction product can, for example, be precipitated with water, and suitably, care is taken that the acid is neutralized.

According to tests so far available, the yield of process product is about 90% of theory. It can be possibly be further increased by optimizing the process parameters.

It is very surprising for one skilled in the art that the progesterone derivatives of the general formula I can be produced by direct Grignardation of the nitriles of the general formula II.

In 1959, P. de Ruggieri et al. had already produced 17alpha-hydroxy-pregnan-20-one derivatives from cyanohydrins of 17-oxosteroids. For this purpose, they had etherified the 17-hydroxy group of the cyanohydrin by reaction with 2,3-dihydropyran and then they reacted the 17-tetrahydropyranyl ether with a Grignard reagent of formula III. The direct Grignardation of unprotected cyanohydrins is not possible in the opinion of the authors, since the Grignard reagent leads to the dissociation of the cyanohydrin, and the initial ketone results, which forms the corresponding methyl carbinol with the Grignard reagent. (J. Amer. Chem. Soc., 81, 1959, p. 5725).

Also, L. F. Fieser et al. (L. F. Fieser and M. Fieser, "Steroids" Verlag Chemie, Weinheim DE, 1961, p. 742) and E. Oliveto (J. Fried and J. E. Edwards (Ed) "Organic Reactions in Steroid Chemistry" Vol. II; Van Nostrand Reinhold Comp. New York et at. 1972, p. 132) have held the view that the direct Grignardation of unprotected cyanohydrins is not possible When syntheses of this type were performed, cyanohydrins were always used even more recently as initial substances, whose 17-hydroxy group was protected. See, for example, K. Annen et at. DE-A 34 27 486
I. Nitta et al. Bull Chem. Soc., Jpn. 58, 1985, 978
V. H. van Rhennen U.S. Pat. No. 4,500,461
J. V. M. Batist et al. EP-A 0263569 and
A. E. V. Popova et al., ref. C. A. 102, 1985, 167.005e The advantages of the process according to the invention lie not only in that a reaction step is saved, they also lie in the very simple feasibility of the process according to the invention and the high yields of process products.

The following embodiment is used to explain in more detail the process according to the invention:

EXAMPLE 100 l of tetrahydrofuran is distilled off from 219 l of a 3 molar solution of methylmagnesium chloride in tetrahydrofuran under nitrogen at standard pressure. Then, 725 l of toluene is added to the mixture so that the temperature does not fall below 80° C. and 300 l of the tetrahydrofuran-toluene mixture is distilled off.

The solution is allowed to cool to 0° C., it is mixed with stirring within 30 minutes with a suspension of 50 kg of 3,3-ethylenedioxy-17beta-5-androsten-17alpha-ol in 150 l of toluene, and the temperature is not to exceed 5° C., and it is stirred for another hour at 5° C.

Then, a solution of 25 kg of ammonium chloride in 200 l of water is added to the reaction mixture so that the reaction temperature does not exceed 80° C., it is acidified with hydrochloride acid up to a pH of 6.5, heated for 20 minutes with stirring to 80° C., the organic phase is separated, the aqueous phase is washed with 200 l of toluene, the organic phases are combined, they are mixed with 200 l of water and the toluene is distilled off by steam distillation.

After the cooling of the reaction mixture, the precipitated intermediate product is filtered off, washed with water, introduced in 500 l of methanol, mixed with 6.5 l of concentrated hydrochloric acid and refluxed for 15 minutes. Then, the mixture is allowed to cool, it is put into a solution of 12.5 kg of sodium acetate in 25 l of water, 400 l of methanol is distilled off and the residue is slowly mixed with 500 l of water.

The precipitated product is filtered off, washed with water and dried at 50° C. in a circulating drying oven.

48 kg of 17alpha-hydroxy-4-pregnene-3,20-dione with the melting point of 210°-213° C. is thus obtained. (Purity of 93% according to HPCL.)

We claim:

1. Process for the production of progesterone derivatives of general formula I

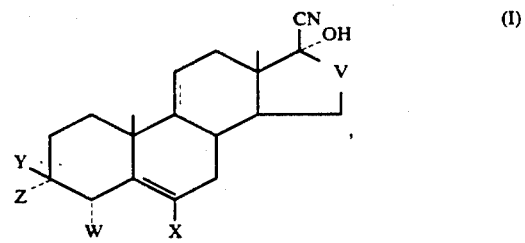

in which

‒‒‒‒‒ symbolizes a single bond or a double bond,

X represents a hydrogen atom, a fluorine atom or a methyl group and

V means a methylene group, an ethylene group, an ethylidene group or a vinylidene group, which is characterized in that a nitrile of the general formula II

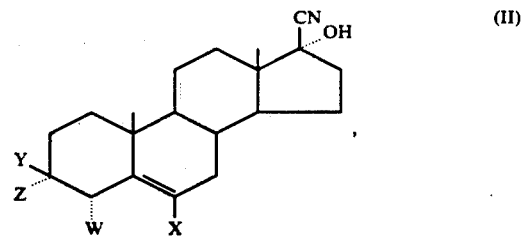

in which Y and Z together are an alkylenedioxy group with 2 to 6 carbon atoms and ‒‒‒, X and V have the above-mentioned meaning and in which W represents a hydrogen atom or in which Y symbolizes an alkyloxy group with up to 4 carbon atoms, a benzyl group or an acyloxy group with 2 to 8 carbon atoms, and Z and W represent two hydrogen atoms or together mean a carbon-carbon bond, with a Grignard reagent of the general formula III $$CH_3-Mg-Z \qquad (III),$$

in which Z symbolizes a chlorine atom or a bromine atom, is reacted and the intermediate products formed are hydrolyzed by acids.

2. Process for the production of progesterone derivatives of general formula I according to claim 1, wherein the reaction is performed with a solution of a complex of the Grignard reagent with an ether in toluene.

3. Process for the production of progesterone derivatives of general formula I according to claim 1, wherein the reaction is performed at a temperature of $-20°$ C. to $+10°$ C.

4. Process for the production of progesterone derivatives of general formula I according to claim 2, wherein the reaction is performed at a temperature of $-20°$ C. to $+10°$ C.

* * * * *